United States Patent
Chan

(10) Patent No.: US 10,555,881 B2
(45) Date of Patent: Feb. 11, 2020

(54) STABILIZATION OF NONIONIC POLYSACCHARIDES WITH BUTYLENE GLYCOL

(71) Applicant: L'OREAL, Paris (FR)

(72) Inventor: David Chan, Edison, NJ (US)

(73) Assignee: L'Oreal, Paris (FR)

( * ) Notice: Subject to any disclaimer, the term of this patent is extended or adjusted under 35 U.S.C. 154(b) by 34 days.

(21) Appl. No.: 15/443,781

(22) Filed: Feb. 27, 2017

(65) Prior Publication Data
US 2018/0243188 A1 Aug. 30, 2018

(51) Int. Cl.
| | |
|---|---|
| *A61K 8/34* | (2006.01) |
| *A61K 8/73* | (2006.01) |
| *A61K 8/49* | (2006.01) |
| *A61K 8/06* | (2006.01) |
| *A61K 8/894* | (2006.01) |
| *A61K 8/60* | (2006.01) |
| *A61K 8/86* | (2006.01) |
| *A61K 8/891* | (2006.01) |
| *A61Q 17/04* | (2006.01) |

(52) U.S. Cl.
CPC .............. *A61K 8/345* (2013.01); *A61K 8/064* (2013.01); *A61K 8/4973* (2013.01); *A61K 8/60* (2013.01); *A61K 8/73* (2013.01); *A61K 8/731* (2013.01); *A61K 8/732* (2013.01); *A61K 8/737* (2013.01); *A61K 8/86* (2013.01); *A61K 8/891* (2013.01); *A61K 8/894* (2013.01); *A61Q 17/04* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 5,425,939 A * | 6/1995 | Guerrero | A61K 8/67 424/401 |
| 7,514,496 B2 | 4/2009 | Amalric et al. | |
| 2003/0118618 A1 * | 6/2003 | Fogel | A61K 8/064 424/401 |

FOREIGN PATENT DOCUMENTS

WO 2004028501 A1 4/2004

* cited by examiner

*Primary Examiner* — Bethany P Barham
*Assistant Examiner* — Barbara S Frazier
(74) *Attorney, Agent, or Firm* — RatnerPrestia

(57) ABSTRACT

A composition is provided, including an emulsion of an aqueous phase in a lipophilic phase, wherein the composition includes water, more than 8 wt % butylene glycol, one or more nonionic polysaccharides, and one or more lipophilic materials. The composition may be prepared by a method including the steps of a) mixing the one or more lipophilic materials with an aqueous mixture including water, the one or more nonionic polysaccharides, and the butylene glycol at a temperature in a range from 30 to 70° C. until homogeneity is reached; b) cooling the product of step a) to room temperature; and optionally c) adding ethanol and/or aluminum starch octenylsuccinate to the product of step b) with mixing. A method of caring for a keratin material in an animal includes applying an effective amount of the composition to the keratin material.

25 Claims, No Drawings

STABILIZATION OF NONIONIC POLYSACCHARIDES WITH BUTYLENE GLYCOL

FIELD OF THE INVENTION

The invention relates to water-in-oil emulsions comprising nonionic polysaccharides in the aqueous phase.

BACKGROUND OF THE INVENTION

Water-in-oil emulsions employing polysaccharides in the aqueous phase are useful in a broad range of cosmetic compositions. The polysaccharides may be used to thicken or gel the aqueous phase, providing suitable application properties for the cosmetic. Nonionic polysaccharides in particular may provide other benefits such as skin softening and reduction in shine when applied to skin. However, water-in-oil emulsions comprising nonionic polysaccharides in the aqueous phase typically have reduced stability relative to emulsions employing the more broadly used anionic and anionically modified polysaccharides, when exposed to temperature extremes such as seen during freezing and thawing cycles. Thus, methods and compositions capable of providing good freeze-thaw stability to water-in-oil emulsions comprising nonionic polysaccharides would be a welcome advance in the cosmetic arts.

SUMMARY OF THE INVENTION

The invention provides a composition comprising an emulsion of an aqueous phase in a lipophilic phase, wherein the composition comprises water, more than 8 wt % butylene glycol, one or more nonionic polysaccharides, and one or more lipophilic materials. The one or more lipophilic materials in total may for example be present in a range from 25 wt % to 50 wt %.

The one or more nonionic polysaccharides may comprise at least one polysaccharide selected from the group consisting of *sclerotium* gum, guar, cellulose, and functionalized celluloses.

The one or more nonionic polysaccharides in total may be present in a range from 0.2 wt % to 0.8 wt %.

The butylene glycol may be present in a range from 10 wt % to 30 wt %.

The composition may further comprise glycerol, which for example may be present in a range from 2 wt % to 5 wt %.

The composition may further comprise ethanol, which for example may be present in a range from 1 wt % to 5 wt %.

The composition may further comprise one or more emulsifiers, which for example may be present in a range from 1.5 wt % to 3 wt %. The one or more emulsifiers may for example comprise one or more selected from the group consisting of methyl glucose sesquistearate, PEG-30 dipolyhydroxystearate, and sorbitan isostearate. The one or more emulsifiers may have an HLB value in a range from 4 to 8.

The one or more lipophilic materials may comprise one or more emollients selected from the group consisting of isopropyl myristate, oleyl erucate, tocopherol, silicones, silicone polymers, caprylic/capric triglyceride, dicaprylyl ether, dicaprylyl carbonate, octyldodecanol, and oils. The one or more emollients in total may for example be present in a range from 2 wt % to 30 wt %. The silicone or silicone polymer may for example comprise one or more selected from the group consisting of dimethicone, PEG-9 polydimethylsiloxyethyl dimethicone, bis-PEG/PPG-14/14 dimethicone, vinyl dimethicone/methicone silsesquioxane crosspolymer, and dimethicone/vinyl dimethicone crosspolymer.

The one or more lipophilic materials may comprise one or more lipophilic sunscreens that in total constitute from 10 wt % to 30 wt % of the composition. The one or more lipophilic sunscreens may for example comprise one or more sunscreens selected from the group consisting of octocrylene, butyl methoxydibenzoylmethane, homosalate, ethylhexyl salicylate, and combinations thereof.

The composition may further comprise an aesthetic modifier, for example aluminum starch octenylsuccinate, a methyl methacrylate crosspolymer, or a combination thereof.

The composition, if subjected to freeze-thaw testing, preferably shows no visible formation of agglomerates or separate layers.

A method of caring for a keratin material in an animal comprises applying to the keratin material an effective amount of any composition according to the invention. For example, the keratin material may be skin.

Compositions according to the invention may be prepared by a method comprising the steps of
  a) mixing the one or more lipophilic materials with an aqueous mixture comprising water, the one or more nonionic polysaccharides, and the butylene glycol at a temperature in a range from 30 to 70° C. until homogeneity is reached;
  b) cooling the product of step a) to room temperature; and optionally
  c) adding ethanol and/or aluminum starch octenylsuccinate to the product of step b) with mixing.

The invention provides a method for improving stability of a composition comprising an emulsion of an aqueous phase in a lipophilic phase, comprising mixing one or more nonionic polysaccharides with an effective amount of butylene glycol, whereby the resulting composition comprises water, more than 8 wt % butylene glycol, one or more nonionic polysaccharides, and one or more lipophilic materials. The resulting composition may, if subjected to freeze-thaw testing, show no visible formation of agglomerates or separate layers.

DETAILED DESCRIPTION OF THE INVENTION

Compositions according to the invention are water-in-oil emulsions in which an aqueous phase comprising a nonionic polysaccharide and butylene glycol are dispersed in a continuous oily or lipophilic phase. Unless stated otherwise, all wt % figures herein are relative to the total composition.

The inventors have found that high concentrations of traditional freezing point depressing materials commonly used to prevent product freezing can decrease the freeze-thaw stability of water-in-oil emulsions employing nonionic polysaccharides, such that phase separation or generation of agglomerates is experienced. Both of these negatively affect the aesthetics of the product. The inventors now disclose that the presence of an effective amount of butylene glycol can provide excellent freeze-thaw stability of water-in-oil emulsions comprising nonionic polysaccharides. At the same time, these compositions have been found to have a better skin feel that provides extra "slip" upon application while avoiding a tacky or sticky feeling.

Although the inventors evaluated other diols, including propylene glycol, which has a lower freezing point (−59° C.) than butylene glycol (−50° C.), it was surprisingly found that only compositions comprising butylene glycol were suitably effective at providing freeze-thaw stability of compositions comprising nonionic polysaccharides. Even increasing the amount of propylene glycol failed to produce a stable product; see composition 86 in Table 1b. Also surprising was that, as seen in the Examples, butylene glycol-containing compositions that passed the freeze-thaw stability test had a lower degree of theoretical freezing point depression, calculated by the Van't Hoff equation, than some of the compositions that contained no butylene glycol and that failed the test. The special effectiveness of butylene glycol was surprising in view of the fact that compositions comprising it were not the ones with the greatest freezing point depression, yet they provided surprisingly better freeze-thaw stability.

In addition to the required nonionic polysaccharide(s), compositions according to the invention may include anionic or cationic polyelectrolytes and/or anionic or cationic polymers. Examples of anionic polymers for this purpose include anionic polysaccharides, such as carboxymethyl cellulose salts, alginates, gellans, agar, and carrageenan. Other examples include polymers bearing multiple sulfonic acid salt groups, for example, polymers comprising repeat units of 2-methyl-[(1-oxo-2-propenyl)amino]-1-propanesulphonic acid (AMPS) in salt form.

Examples of cationic polymers include polymers, for example, polysaccharides bearing multiple quaternary ammonium groups. Other examples include polymers bearing multiple $NH_2$ or substituted amine groups. These can become polycationic under certain pH conditions. In some preferred embodiments, however, any or all anionic polymers, cationic polymers, anionic polyelectrolytes, and/or cationic polyelectrolytes, anionic or cationic polysaccharides (e.g., anionically or cationically modified starches) may be excluded from the compositions.

Electrolytes capable of gelling anionic or cationic polymers or polyelectrolytes may be included in the compositions, for example, calcium ions or phosphate ions. Or any or all such electrolytes may be excluded.

Other polymers may also be included, for example, (co)polymers comprising vinylpyrrolidone repeat units, methyl vinyl ether repeat units, vinyl ester repeat units, or (meth)acrylic acid, amide, and/or ester repeat units. Any of these polymers may be water-soluble, or lipid soluble, or they may be insoluble in either or both of these, for example by virtue of being crosslinked. However, any or all of the foregoing polymers, for example acrylic acid (co)polymers or copolymers comprising repeat units of AMPS, may instead be excluded from the compositions.

Aqueous Phase

The water-in-oil compositions of the invention may comprise at least about 30, 35, 40 or 45 wt % water. They may comprise at most about 60, 55 or 53 or 50 wt % water. In addition to water, the aqueous phase includes one or more nonionic polysaccharides. Suitable examples of nonionic polysaccharides include galactomannan, guar gum, carob bean gum, hydroxypropyl guar, starches, scleroglucan gum, konjac, xanthan gum, cellulose, and functionalized celluloses, for example hydroxyethylcellulose and hydroxypropyl methylcellulose.

Nonionic natural gums are one preferred class of the nonionic polysaccharides. An especially useful nonionic natural gum is *sclerotium* gum, which provides a thickening or gelling effect while providing cosmetic benefits such as skin softening and reduction in shine. The one or more nonionic polysaccharides, either individually or in combination, may be present in an amount of at least about 0.1, 0.15, 0.2, 0.25, 0.3, 0.35, or 0.4 wt %. The amount may be at most about 1, 0.9, 0.8, 0.7, or 0.6 wt %. For example, the amount may be from 0.1 to 1 wt %, or from 0.15 to 1 wt %, or from 0.2 to 0.9 wt %, or from 0.25 to 0.9 wt %, or from 0.2 to 0.8 wt %, or from 0.3 to 0.8 wt %, or from 0.35 to 0.7 wt %, or from 0.4 to 0.6 wt %.

Butylene glycol is included in an amount that, either alone or in combination with other ingredients such as glycerol, ethanol, and/or other diols, is effective to produce freeze-thaw stability of the water-in-oil compositions as defined in the Examples. At least about 4, 5, 6, 7, 8, 9, or 10 wt % of butylene glycol may be used. The amount may be at most about 30, 20, 17, 15, or 13 wt %. For example, the amount may be from 4 to 30 wt %, or from 5 to 30 wt %, or from 6 to 30 wt %, or from 8 to 30 wt %, or from 10 to 30 wt %, or from 8 to 20 wt %, or from 10 to 20 wt %, or from 8 to 15 wt %, or from 10 to 15 wt %.

Glycerol may suitably be included, for example, at a level of at least about 1, 1.5, 2, 3, 4, or 5 wt %. The amount may be at most about 10, 9, 8, 7, or 6 wt %. For example, it may be present from 1 to 10 wt %, or from 1.5 to 10 wt %, or from 2 to 10 wt %, or from 2 to 5 wt %, or from 3 to 10 wt %, or from 3 to 9 wt %, or from 4 to 8 wt %, or from 5 to 7 wt %.

Ethanol may suitably be included, for example, at a level of at least about 1, 1.5, 2, 3, 4, or 5 wt %. The amount may be at most about 10, 9, 8, 7, 6, or 5 wt %. In some cases, the amount may be more limited such that the composition comprises less than about 4, 3, 2, or 1 wt % ethanol, or none at all. For example, it may be present at from 1 to 10 wt %, or from 1 to 7 wt %, or from 1 to 5 wt %, or from 2 to 10 wt %, or from 3 to 9 wt %, or from 3 to 8 wt %, or from 3 to 7 wt %, or from 4 to 8 wt %, or from 5 to 10 wt %.

Propylene glycol may suitably be included, for example, at a level of at least about 1, 1.5, 2, 3, 4, or 5 wt %. The amount may be at most about 10, 9, 8, 7, or 6 wt %. In some cases, the amount may be more limited such that the composition comprises less than about 4, 3, 2, or 1 wt % propylene glycol, or none at all.

1,3-Propanediol may suitably be included, for example, at a level of at least about 1, 1.5, 2, 3, 4, or 5 wt %. The amount may be at most about 10, 9, 8, 7, or 6 wt %. In some cases, the amount may be more limited such that the composition comprises less than about 4, 3, 2, or 1 wt % 1,3-propanediol, or none at all.

Lipophilic or Oily Phase

The lipophilic or oily phase comprises one or more lipophilic materials. The term "lipophilic material" means any water-immiscible cosmetic or dermatological organic compound that may be completely dissolved in molecular form in a liquid fatty phase, or that may be dissolved in colloidal form (for example, in micellar form) in a liquid fatty phase.

Examples of suitable lipophilic materials include antibacterial agents, antifungal agents, anti-seborrheic agents, anti-acne agents, keratolytic agents, cicatrizing agents, pigmentation modifiers, tanning accelerators, artificial tanning agents, liporegulators, anti-ageing and anti-wrinkle agents, emollients, refreshing agents, vascular protectors, insect repellents, deodorants, antidandruff agents, hair-loss counteractants, essential oils, fragrances, sunscreens, antioxidants, free-radical scavengers, moisturizers, fatty substances that are liquid at room temperature (oils), fatty substances that are solid at room temperature (waxes), fatty substances that are semi-solid at room temperature, such as pasty fatty substances or butters, and mixtures thereof.

Exemplary emollients include one or more compounds selected from the group consisting of isopropyl myristate, oleyl erucate, tocopherol, silicones, silicone polymers, caprylic/capric triglyceride, dicaprylyl ether, dicaprylyl carbonate, octyldodecanol, and oils. If present, emollients may in total typically constitute in a range from 2 wt % to 30 wt % of the composition, although amounts above or below this range may be used as well. For example, they may constitute from 3 to 20 wt % or from 4 to 15 wt %, or from 4 to 10 wt %, or from 5 to 15 wt %, or from 5 to 10 wt %.

Specific examples of suitable lipophilic materials include: ceramides, essential fatty acids, vitamins such as vitamin A (retinol) or esters thereof, vitamin E or esters thereof such as tocopheryl acetate, vitamin D or derivatives thereof and vitamin F or derivatives thereof, carotenes such as β-carotene and derivatives thereof such as lycopene, salicylic acid derivatives, especially those described in documents FR-A-2 581 542, EP-A-378 936 and EP-A-570 230, lipophilic sunscreens, for instance triazine derivatives, dibenzoyl methane derivatives or benzophenones, essential oils, which may be chosen especially from *eucalyptus* oil, lavandin oil, lavender oil, vetiver oil, *Litsea cubeba* oil, lemon oil, orange oil, sandalwood oil, rosemary oil, camomile oil, savory oil, nutmeg oil, cinnamon oil, hyssop oil, caraway oil, mandarin oil, juniper oil, clove oil, bergamot oil, geranium oil, cade oil, ginger oil, carrot oil, lemon grass oil, rose oil, fennel oil, thyme oil and peppermint oil, and mixtures thereof.

The lipophilic or oily phase as a whole may be liquid at room temperature (e.g., 20 or 25° C.), although it may contain some solid components dispersed in it. For example, it may contain a particulate organic polymer, for example, a methyl methacrylate crosspolymer. If a particulate organic polymer is included, it may constitute at least about 1 or 2 wt % of the composition. It may constitute at most about 10, 7 or 5 wt %.

The lipophilic phase of water-in-oil compositions of the invention may constitute at least about 25, 27, or 30 wt % of the composition. It may constitute at most about 50, 45, 40 or 35 wt % of the composition.

For example, the content may be from 25 to 50 wt %, or from 25 to 45 wt %, or from 26 to 40 wt %, or from 26 to 35 wt %. These ranges may apply to the lipophilic phase as a whole, including any solid components dispersed in it. Alternatively, they may apply to the total of the one or more lipophilic materials in the lipophilic or oily phase.

Any of a wide variety of lipophilic materials may be present in the oily phase. For example, the oily phase may comprise silicone-based materials, such as silicones and silicone-containing polymers. These may include silicone oils such as volatile or non-volatile polydimethylsiloxanes (PDMSs) having a linear or cyclic silicone chain, which are liquid or pasty at room temperature, especially volatile silicone oils, for example, cyclopolydimethylsiloxanes (cyclomethicones) such as cyclohexadimethylsiloxane and cyclopenta-dimethylsiloxane; polydimethylsiloxanes comprising alkyl, alkoxy or phenyl groups, pendant or at the end of a silicone chain, these groups having from 2 to 24 carbon atoms; phenylsilicones such as phenyl trimethicones, phenyl dimethicones, phenyltrimethyl-siloxydiphenylsiloxanes, diphenyl dimethicones, diphenylmethyldiphenyltrisiloxanes, 2-phenylethyl trimethylsiloxysilicates, polymethylphenylsiloxanes, and combinations thereof. In some embodiments, preferred examples include dimethicone, PEG-9 polydimethylsiloxyethyl dimethicone, bis-PEG/PPG-14/14 dimethicone, vinyl dimethicone/methicone silsesquioxane crosspolymer, and dimethicone/vinyl dimethicone crosspolymer.

The oily phase may also comprise hydrocarbon-based materials. Examples include hydrocarbon-based oils of animal origin, such as perhydrosqualene. Synthetic examples include linear or branched hydrocarbons of mineral or synthetic origin, such as volatile or non-volatile liquid paraffins and derivatives thereof, petroleum jelly, polydecenes, isohexadecane, isododecane and hydrogenated polyisobutene.

The oily phase may comprise mono-, di-, or tri-glycerides, fatty acid esters, fatty acids, fatty acid amides, fats, natural oils, or derivatives thereof. Examples include synthetic esters and ethers of fatty acids, such as the oils of formulae $R^1COOR^2$ and $R^1OR^2$, in which $R^1$ represents a fatty acid residue having from 8 to 29 carbon atoms and $R^2$ represents a branched or unbranched hydrocarbon-based chain having from 3 to 30 carbon atoms, such as purcellin oil, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate. Other examples include isopropyl myristate, oleyl erucate, caprylic/capric triglyceride, and moisturizers (e.g., butyrospermum parkii (shea) butter).

Specific nonlimiting examples of suitable oils include esters derived from the reaction of at least one fatty acid having at least 6 carbon atoms, for example, from 6 to 26 carbon atoms, from 6 to 20 carbon atoms, or from 6 to 16 carbon atoms, and of at least one alcohol having from 1 to 17 carbon atoms, for example, from 3 to 15 carbon atoms; mention may be made especially of isopropyl myristate, isopropyl palmitate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols having 12 or 13 carbon atoms, dicaprylyl carbonate, fatty acid ethers having from 6 to 20 carbon atoms such as dicaprylyl ether, glyceryl ethers having from 6 to 12 carbon atoms, for instance 2-ethylhexyl glyceryl ether (INCI name: ethylhexylglycerin), volatile linear alkanes, advantageously of plant origin, having from 7 to 17 carbon atoms, from 9 to 15 carbon atoms, or from 11 to 13 carbon atoms. As examples of volatile linear alkanes that are suitable for use in the invention, mention may be made of those described in WO 2007/068,371. As examples of volatile linear alkanes that are suitable for use in the invention, mention may be made of n-nonane, n-decane, n-undecane, n-dodecane, n-tridecane, n-tetradecane, n-pentadecane, n-hexadecane, n-heptadecane, and mixtures thereof.

The oily phase may comprise one or more organic sunscreens. Nonlimiting examples include lipophilic sunscreens, for example octocrylene, butyl methoxydibenzoylmethane (avobenzone), oxybenzone, homosalate, and ethylhexyl salicylate. When present, the one or more organic sunscreens may in total constitute at least about 1, 5, 10, 15 or 20 wt % of the composition. They may constitute at most about 35, 30 or 25 wt %. For example, they may constitute from 1 to 30 wt %, or from 5 to 30 wt %, or from 10 to 30 wt %, or from 15 to 25 wt %, or from 20 to 25 wt %.

Emulsifiers

The emulsion of the aqueous phase in the lipophilic or oily phase may be stabilized by one or more suitable emulsifiers. Nonlimiting examples of suitable emulsifier types include acyl lactylates, alkyl phosphates, carboxylic acid copolymers, esters and ethers of glucose, esters of glycerin, esters of propylene glycol, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps and mixtures thereof. Nonlimiting examples of suitable emulsifiers include octyldodecanol, methyl glucose sesquistea rate, PEG-30 dipolyhydroxystearate, sorbitan isostea rate, ceteareth-20, ceteth-10, cetyl phosphate, diethanolamine cetyl phosphate, glyceryl stearate, PEG-100 stearate, polyethylene glycol 20 sorbitan monolaurate, polyethylene glycol 5 soya sterol, polysorbate 60, polysorbate 80, potassium cetyl phosphate, PPG-2 methyl glucose ether distearate, steareth-20, and mixtures thereof. Suitable emulsifiers typically have an HLB value in a range from 4 to 8. Typically, the one or more emulsifiers in total will constitute at least 1.0 wt % of the composition, or at least 1.5 wt %. Typically, they will constitute at most 4%, or at most 3% or 2%. For example, they may total from 1.0 to 4 wt %, or from 1.0 to 3 wt %, or from 1.0 to 2 wt %, or from 1.5 to 4 wt %, or from 1.5 to 3 wt %, or from 1.5 to 2 wt %.

Auxiliary Ingredients

The compositions of the invention may also include, in the aqueous phase and/or the oily phase, any of a variety of auxiliary ingredients or additives (e.g., preservatives). Nonlimiting examples of the auxiliary ingredients include colorants, odorants, vitamins (e.g., tocopherol), and preservatives. Nonlimiting examples of the preservatives include chlorphenesin, phenoxyethanol, and caprylyl glycol. If present, the preservative(s) will typically constitute from 0.5 wt % to 3 wt % of the composition. A chelating agent such as disodium EDTA, if included, will typically constitute from 0.05 wt % to 0.15 wt % of the composition. One or more aesthetic modifiers, for example aluminum starch octenylsuccinate and/or a methyl methacrylate crosspolymer may be included. If present, aluminum starch octenylsuccinate will typically constitute from 0.3 wt % to 1 wt % of the composition. A typical content of methyl methacrylate crosspolymer is in a range from 1 to 5 wt %. Ethanol, typically in the form of "denatured alcohol," may be included. One or more artificial tanning agents may be included. Compositions of the invention may include physical blocker sunscreens, for example cerium oxides, chromium oxides, cobalt oxides, iron oxides, red petrolatum, silicone-treated titanium dioxide, titanium dioxide, zinc oxide, zirconium oxide, or mixtures thereof. When a given auxiliary ingredient is included, it may constitute at most about 2, 1.5, 1.0, 0.7, 0.5, 0.3, 0.2, or 0.1 wt % of the composition.

Compositions according to the invention may be used in a method for caring for a keratin material in an animal, for example, a human or other mammal. Such a method comprises applying to the keratin material an amount of the composition effective to provide a desired benefit, for example, softening, detangling, coloring, or protecting against damage by sun or other insults. The keratin material may be hair, nails, and/or skin.

Making the Composition

Typically, compositions of the invention can be made by a process comprising the steps of
a) mixing the one or more lipophilic materials with an aqueous mixture comprising water, the one or more nonionic polysaccharides, and the butylene glycol at a temperature in a range from 30 to 70° C. until homogeneity is reached;
b) cooling the product of step a) to room temperature; and optionally
c) adding ethanol and/or aluminum starch octenylsuccinate to the product of step b) with mixing.

EXAMPLES

Compositions were prepared by blending lipophilic materials (including sunscreens and emollients), typically at 50° C. or the melting temperature of the highest melting point lipophilic material, and adding the blend with agitation to a mixture of water and any preservatives, chelating agents, non-ionic polysaccharide, glycols and glycerol to be included at room temperature to form a homogeneous emulsion, followed by adding a final phase of any remaining raw materials, such as aesthetic modifiers (aluminum starch octenylsuccinate) and ethanol.

Freeze-thaw testing to confirm freeze-thaw stability was conducted as follows. Each composition was evaluated for freeze-thaw stability by subjecting it to repeated freeze-thaw cycles of holding the composition at −20° C. for 12 h and then at 25° C. for 12 h. Assessments were performed at days 5 and 10, with the day 10 assessment being determinative of stability for purposes of the invention. A composition was judged freeze-thaw stable if it showed no visibly separate layers and no visible agglomerates, when viewed by the unaided eye at the end of day 10 (i.e., ten freeze-thaw cycles). The results of freeze-thaw testing for a number of compositions are shown in Tables 1a and 1b, along with theoretical freezing point depressions for each composition calculated according to the Van't Hoff Equation.

Compositions 90 and 89a were stable and are according to the invention, while the remainder of the compositions failed the stability test and are comparative examples.

TABLE 1a

|  | Ingredient | Examples |  |  |  |  |  |  |  |  |  |
|---|---|---|---|---|---|---|---|---|---|---|---|
|  |  | 90 | 89 | 89A | 89B | 89C | 89D | 89E | 89F | 89G | 89H |
| Sunscreens | BUTYL METHOXY-DIBENZOYLMETHANE | 3 | 3 | 3 | 3 | 3 | 3 | 3 | 3 | 3 | 3 |
|  | OCTOCRYLENE | 6 | 6 | 6 | 6 | 6 | 6 | 6 | 6 | 6 | 6 |
|  | ETHYLHEXYL SALICYLATE | 3 | 3 | 3 | 3 | 3 | 3 | 3 | 3 | 3 | 3 |
|  | HOMOSALATE | 10 | 10 | 10 | 10 | 10 | 10 | 10 | 10 | 10 | 10 |
| Surfactants | METHYL GLUCOSE SESQUISTEARATE | 0.4 | 0.4 | 0.4 | 0.4 | 0.4 | 0.4 | 0.4 | 0.4 | 0.4 | 0.4 |
|  | PEG-30 DIPOLYHYDROXYSTEARATE | 1 | 0.8 | 0.8 | 0.8 | 0.8 | 0.8 | 0.8 | 0.8 | 0.8 | 0.8 |
|  | SORBITAN ISOSTEARATE | 0.4 | 0.4 | 0.4 | 0.4 | 0.4 | 0.4 | 0.4 | 0.4 | 0.4 | 0.4 |
| Emollients | ISOPROPYL MYRISTATE | 2.5 | 2.5 | 2.5 | 2.5 | 2.5 | 2.5 | 2.5 | 2.5 | 2.5 | 2.5 |
|  | CAPRYLIC/CAPRIC TRIGLYCERIDE | 1.5 | 1.75 | 1.75 | 1.75 | 1.75 | 1.75 | 1.75 | 1.75 | 1.75 | 1.75 |

TABLE 1a-continued

| | Ingredient | \multicolumn{10}{c}{Examples} | | | | | | | | | |
| --- | --- | --- | --- | --- | --- | --- | --- | --- | --- | --- | --- |
| | | 90 | 89 | 89A | 89B | 89C | 89D | 89E | 89F | 89G | 89H |
| | OCTYLDODECANOL | 0.5 | 0.5 | 0.5 | 0.5 | 0.5 | 0.5 | 0.5 | 0.5 | 0.5 | 0.5 |
| | BUTYROSPERMUM PARKII (SHEA) BUTTER | | | | | | | | | | |
| | CAPRYLYL GLYCOL | 0.3 | 0.3 | 0.3 | 0.3 | 0.3 | 0.3 | 0.3 | 0.3 | 0.3 | 0.3 |
| | TOCOPHEROL | | | | | | | | | | |
| | HYDROGENATED PALM GLYCERIDES CITRATE | | | | | | | | | | |
| | OLEYL ERUCATE | | | | | | | | | | |
| | DIMETHICONE | 0.03 | 0.03 | 0.03 | 0.03 | 0.03 | 0.03 | 0.03 | 0.03 | 0.03 | 0.03 |
| | DIMETHICONE | | | | | | | | | | |
| | BIS-PEG/PPG-14/14 DIMETHICONE | 0.17 | 0.17 | 0.17 | 0.17 | 0.17 | 0.17 | 0.17 | 0.17 | 0.17 | 0.17 |
| | PEG-9 POLYDIMETHYL-SILOXYETHYL DIMETHICONE | 0.2 | 0.2 | 0.2 | 0.2 | 0.2 | 0.2 | 0.2 | 0.2 | 0.2 | 0.2 |
| | DIMETHICONE/VINYL DIMETHICONE CROSSPOLYMER | | | | | | | | | | |
| | VINYL DIMETHICONE/ METHICONE SILSESQUIOXANE CROSSPOLYMER | 1 | 1 | 1 | 1 | 1 | 1 | 1 | 1 | 1 | 1 |
| Aesthetic modifiers | ALUMINUM STARCH OCTENYLSUCCINATE | 0.645 | 0.645 | 0.645 | 0.645 | 0.645 | 0.645 | 0.645 | 0.645 | 0.645 | 0.645 |
| | ALCOHOL DENAT. | 3 | 3 | 3 | 3 | 3 | 3 | 3 | 3 | 3 | 3 |
| | METHYL METHACRYLATE CROSSPOLYMER | 3 | 3 | 3 | 3 | 3 | 3 | 3 | 3 | 3 | 3 |
| Nonionic Polysaccharides | SCLEROTIUM GUM | 0.4 | 0.4 | 0.4 | 0.4 | 0.4 | 0.4 | 0.4 | 0.4 | 0.4 | 0.4 |
| Freeze-thaw Stabilizers | BUTYLENE GLYCOL | 10 | 5 | 10 | 10 | 6 | 8 | 6 | 8 | 8 | 8 |
| | PROPANEDIOL | | | | | | | | | 4 | |
| | GLYCERIN | 2 | 2 | 2 | | | 2 | 2 | | | |
| | PROPYLENE GLYCOL | | | 4 | 4 | | | | 4 | 4 | |
| Preservatives and Preservative Boosters | CHLORPHENESIN | 0.2 | 0.2 | 0.2 | 0.2 | 0.2 | 0.2 | 0.2 | 0.2 | 0.2 | 0.2 |
| | PHENOXYETHANOL | 0.7 | 0.7 | 0.7 | 0.7 | 0.7 | 0.7 | 0.7 | 0.7 | 0.7 | 0.7 |
| | DISODIUM EDTA | 0.099 | 0.099 | 0.099 | 0.099 | 0.099 | 0.099 | 0.099 | 0.099 | 0.099 | 0.099 |
| | CITRIC ACID | | | | | | | | | | |
| | WATER | Q.S. to 100 | Q.S. to 100 | Q.S. to 100 | Q.S. to 100 | Q.S. to 100 | Q.S. to 100 | Q.S. to 100 | Q.S. to 100 | Q.S. to 100 | Q.S. to 100 |
| | Theoretical Freezing Point Depression (° C.) | 4.95 | 4.75 | 7.52 | 3.98 | 3.05 | 3.97 | 4.28 | 5.28 | 5.28 | 3.07 |

TABLE 1b

| | Ingredient | \multicolumn{6}{c}{Examples} | | | | | |
| --- | --- | --- | --- | --- | --- | --- | --- |
| | | 87 | 86 | 85 | 84 | 83 | 82 |
| Sunscreens | BUTYL METHOXY-DIBENZOYLMETHANE | 3 | 3 | 3 | 3 | 3 | 3 |
| | OCTOCRYLENE | 6 | 6 | 6 | 6 | 6 | 6 |
| | ETHYLHEXYL SALICYLATE | 3 | 3 | 3 | 3 | 3 | 3 |
| | HOMOSALATE | 10 | 10 | 10 | 10 | 10 | 10 |
| Surfactants | METHYL GLUCOSE SESQUISTEARATE | 0.4 | 0.4 | 0.4 | 0.4 | 0.4 | 0.4 |
| | PEG-30 DIPOLYHYDROXYSTEARATE | 0.8 | 0.8 | 0.8 | 0.8 | 0.8 | 0.8 |
| | SORBITAN ISOSTEARATE | 0.4 | 0.4 | 0.4 | 0.4 | 0.4 | 0.4 |
| Emollients | ISOPROPYL MYRISTATE | 2.5 | 2.5 | 2.5 | 2.5 | 2.5 | 2.5 |
| | CAPRYLIC/CAPRIC TRIGLYCERIDE | 1.5 | 1.5 | 1.5 | 1.5 | 1.5 | 1.5 |
| | OCTYLDODECANOL | 0.5 | 0.5 | 0.5 | 0.5 | 0.5 | |
| | BUTYROSPERMUM PARKII (SHEA) BUTTER | | | | | | |
| | CAPRYLYL GLYCOL | 0.3 | 0.3 | 0.3 | 0.3 | 0.3 | 0.3 |
| | TOCOPHEROL | | | | | | 0.00006 |
| | HYDROGENATED PALM GLYCERIDES CITRATE | | | | | | 0.00006 |
| | OLEYL ERUCATE | | | | | | 0.49988 |
| | DIMETHICONE | 0.03 | 0.03 | 0.03 | 0.03 | 0.03 | 0.03 |
| | DIMETHICONE | | | | | | |
| | BIS-PEG/PPG-14/14 DIMETHICONE | 0.17 | 0.17 | 0.17 | 0.17 | 0.17 | 0.17 |

TABLE 1b-continued

|  | Ingredient | | | | | | |
|---|---|---|---|---|---|---|---|
| | PEG-9 POLYDIMETHYL-SILOXYETHYL DIMETHICONE | 0.2 | 0.2 | 0.2 | 0.2 | 0.2 | 0.2 |
| | DIMETHICONE/VINYL DIMETHICONE CROSSPOLYMER | | | | | | |
| | VINYL DIMETHICONE/METHICONE SILSESQUIOXANE CROSSPOLYMER | 1 | 1 | 1 | 1 | 1 | 1 |
| Aesthetic modifiers | ALUMINUM STARCH OCTENYLSUCCINATE | 0.645 | 0.645 | 0.645 | 0.645 | 0.645 | 0.645 |
| | ALCOHOL DENAT. | 3 | 3 | 3 | 3 | 3 | 3 |
| | METHYL METHACRYLATE CROSSPOLYMER | 3 | 3 | 3 | 3 | 3 | 3 |
| Nonionic Polysaccharides | SCLEROTIUM GUM | 0.5 | 0.5 | 0.5 | 0.5 | 0.4 | 0.5 |
| Freeze-thaw Stabilizers | BUTYLENE GLYCOL | | | | | | |
| | PROPANEDIOL | 8 | | | | | |
| | GLYCERIN | 2 | 2 | 2 | 2 | 2 | 5 |
| | PROPYLENE GLYCOL | | 13 | 7 | 9 | 9 | 5 |
| Preservatives and Preservative Boosters | CHLORPHENESIN | 0.2 | 0.2 | 0.2 | 0.2 | 0.2 | 0.2 |
| | PHENOXYETHANOL | 0.7 | 0.7 | 0.7 | 0.7 | 0.7 | 0.7 |
| | DISODIUM EDTA | 0.099 | 0.099 | 0.099 | 0.099 | 0.099 | 0.099 |
| | CITRIC ACID | | | | | | |
| | WATER | Q.S. to 100 | Q.S. to 100 | Q.S. to 100 | Q.S. to 100 | Q.S. to 100 | Q.S. to 100 |
| | Theoretical Freezing Point Depression (° C.) | 4.54 | 7.63 | 3.99 | 5.11 | 5.10 | 4.30 |

| | | Examples | | | | |
|---|---|---|---|---|---|---|
| | Ingredient | 81 | 80 | 79 | 78 | 77 |
| Sunscreens | BUTYL METHOXYDIBENZOYLMETHANE | 3 | 3 | 3 | 3 | 3 |
| | OCTOCRYLENE | 6 | 6 | 6 | 6 | 6 |
| | ETHYLHEXYL SALICYLATE | 3 | 3 | 3 | 3 | 3 |
| | HOMOSALATE | 10 | 10 | 10 | 10 | 10 |
| Surfactants | METHYL GLUCOSE SESQUISTEARATE | 0.4 | 0.4 | 0.4 | 0.3 | 0.3 |
| | PEG-30 DIPOLYHYDROXYSTEARATE | 0.8 | 0.8 | 0.8 | 1.2 | 1.2 |
| | SORBITAN ISOSTEARATE | 0.4 | 0.4 | 0.4 | 0.3 | 0.3 |
| Emollients | ISOPROPYL MYRISTATE | 2.5 | 2.5 | 2.5 | 1.75 | 1.75 |
| | CAPRYLIC/CAPRIC TRIGLYCERIDE | 1.5 | 1.5 | 1.5 | 2 | 1.75 |
| | OCTYLDODECANOL | | 0.5 | | 0.2 | 0.3 |
| | *BUTYROSPERMUM PARKII* (SHEA) BUTTER | 0.499995 | | | 0.99999 | |
| | CAPRYLYL GLYCOL | 0.3 | 0.3 | 0.3 | 0.3 | 0.3 |
| | TOCOPHEROL | | | | | |
| | HYDROGENATED PALM GLYCERIDES CITRATE | | | | | |
| | OLEYL ERUCATE | | | | | |
| | DIMETHICONE | 0.03 | 0.03 | 0.03 | 0.03 | 0.03 |
| | DIMETHICONE | | | | | 1.52 |
| | BIS-PEG/PPG-14/14 DIMETHICONE | 0.17 | 0.17 | 0.17 | 0.17 | 0.17 |
| | PEG-9 POLYDIMETHYL-SILOXYETHYL DIMETHICONE | 0.2 | 0.2 | 0.2 | 0.2 | 0.2 |
| | DIMETHICONE/VINYL DIMETHICONE CROSSPOLYMER | | | | | 0.48 |
| | VINYL DIMETHICONE/METHICONE SILSESQUIOXANE CROSSPOLYMER | 1 | 1 | 1 | 1 | |
| Aesthetic modifiers | ALUMINUM STARCH OCTENYLSUCCINATE | 0.645 | 0.645 | 0.645 | 0.645 | 0.645 |
| | ALCOHOL DENAT. | 3 | 3 | 3 | 3 | 3 |
| | METHYL METHACRYLATE CROSSPOLYMER | 3 | 3 | 3 | 3 | 3 |
| Nonionic Polysaccharides | SCLEROTIUM GUM | 0.5 | 0.5 | 0.5 | 0.5 | 0.5 |
| Freeze-thaw Stabilizers | BUTYLENE GLYCOL | | | | | |
| | PROPANEDIOL | | | | | |
| | GLYCERIN | 5 | 5 | 4 | 4 | 5 |
| | PROPYLENE GLYCOL | 5 | 5 | 6 | 6 | 7 |

TABLE 1b-continued

| | | | | | | |
|---|---|---|---|---|---|---|
| Preservatives and Preservative Boosters | CHLORPHENESIN | 0.2 | 0.2 | 0.2 | 0.2 | 0.2 |
| | PHENOXYETHANOL | 0.7 | 0.7 | 0.7 | 0.7 | 0.7 |
| | DISODIUM EDTA | 0.099 | 0.099 | 0.099 | 0.099 | 0.099 |
| | CITRIC ACID | 0.000005 | | | 0.00001 | |
| | WATER | Q.S. to 100 | Q.S. to 100 | Q.S. to 100 | Q.S. to 100 | Q.S. to 100 |
| | Theoretical Freezing Point Depression (° C.) | 4.30 | 4.30 | 4.34 | 4.44 | 5.50 |

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A composition comprising an emulsion of an aqueous phase in a lipophilic phase, wherein the composition comprises 30-60 wt % water, 10-30 wt % butylene glycol, *sclerotium* gum, 1-10 wt % glycerol and one or more lipophilic materials, wherein the lipophilic phase constitutes 25-50 wt % of the composition, and wherein the one or more lipophilic materials comprise one or more emollients selected from the group consisting of isopropyl myristate, caprylic/capric triglyceride, octyldodecanol, caprylyl glycol, dimethicone, bis-PEG/PPG-14/14 dimethicone, PEG-9 polydimethylsiloxyethyl dimethicone, vinyl dimethicone/methicone silsesquioxane crosspolymer, and combinations thereof.

2. The composition according to claim 1, wherein the *sclerotium* gum is present in a range from 0.4 wt % to 0.6 wt %.

3. The composition according to claim 1, wherein the butylene glycol is present in a range from 10 wt % to 15 wt %.

4. The composition according to claim 1, wherein the glycerol is present in a range from 2 wt % to 5 wt %.

5. The composition according to claim 1, further comprising ethanol.

6. The composition according to claim 5, wherein the ethanol is present in a range from 1 wt % to 5 wt %.

7. The composition according to claim 1, further comprising one or more emulsifiers.

8. The composition according to claim 7, wherein the one or more emulsifiers in total are present in a range from 1.5 wt % to 3 wt %.

9. The composition according to claim 1, wherein the one or more emollients are selected from the group consisting of isopropyl myristate, caprylic/capric triglyceride, octyldodecanol, caprylyl glycol and combination thereof.

10. The composition according to claim 1, wherein the one or more emollients in total are present in a range from 5 wt % to 10 wt %.

11. The composition according to claim 1, wherein the one or more lipophilic materials in total are present in a range from 25 wt % to 50 wt %.

12. The composition according to claim 1, wherein the one or more emollients are selected from the group consisting of dimethicone, PEG-9 polydimethylsiloxyethyl dimethicone, bis-PEG/PPG-14/14 dimethicone, vinyl dimethicone/methicone silsesquioxane crosspolymer, and combinations thereof.

13. The composition according to claim 7, wherein the one or more emulsifiers comprise one or more selected from the group consisting of methyl glucose sesquistearate, PEG-30 dipolyhydroxystearate, sorbitan isostearate and combinations thereof.

14. The composition according to claim 7, wherein the one or more emulsifiers have an HLB value in a range from 4 to 8.

15. The composition according to claim 1, wherein the one or more lipophilic materials further comprise one or more lipophilic sunscreens that in total constitute from 10 wt % to 30 wt % of the composition.

16. The composition according to claim 15, wherein the one or more lipophilic sunscreens comprise one or more sunscreens selected from the group consisting of octocrylene, butyl methoxydibenzoylmethane, oxybenzone, homosalate, ethylhexyl salicylate, and combinations thereof.

17. The composition according to claim 1, further comprising an aesthetic modifier.

18. The composition according to claim 17, wherein the aesthetic modifier comprises aluminum starch octenylsuccinate, a methyl methacrylate crosspolymer, or a combination thereof.

19. The composition according to claim 1, wherein the composition, if subjected to freeze-thaw testing, shows no visible formation of agglomerates or separate layers.

20. A method of caring for a keratin material in an animal, comprising applying to the keratin material an effective amount of the composition according to claim 1.

21. The method according to claim 20, wherein the keratin material is skin.

22. A method of preparing the composition according to claim 1, comprising the steps of
   a) mixing the one or more lipophilic materials with an aqueous mixture comprising water, the *sclerotium* gum, the glycerol and the butylene glycol at a temperature in a range from 30 to 70° C. until homogeneity is reached;
   b) cooling the product of step a) to room temperature.

23. A method for improving stability of a composition comprising an emulsion of an aqueous phase in a lipophilic phase, comprising mixing *sclerotium* gum and glycerol with butylene glycol, whereby the resulting composition comprises 30-60 wt % water, 10-30 wt % butylene glycol, *sclerotium* gum, 1-10 wt % glycerol and one or more lipophilic materials, wherein the lipophilic phase constitutes 25-50 wt % of the composition, and wherein the one or more lipophilic materials comprises one or more emollients selected from the group consisting of isopropyl myristate, caprylic/capric triglyceride, octyldodecanol, caprylyl glycol, dimethicone, bis-PEG/PPG-14/14 dimethicone, PEG-9 polydimethylsiloxyethyl dimethicone, vinyl dimethicone/methicone silsesquioxane crosspolymer, and combinations thereof.

24. The method according to claim 23, wherein the composition, if subjected to freeze-thaw testing, shows no visible formation of agglomerates or separate layers.

25. The method of claim 22, further comprising adding ethanol and/or aluminum starch octenylsuccinate to the product of step b) with mixing.

* * * * *